United States Patent [19]

McCoy et al.

[11] Patent Number: 4,806,632

[45] Date of Patent: Feb. 21, 1989

[54] PROCESS FOR THE POST-HYDROGENATION OF SUCROSE POLYESTERS

[75] Inventors: Stephen A. McCoy, Villa Hills, Ky.; David J. Weisgerber; Richard L. Ingle, both of Cincinnati, Ohio

[73] Assignee: The Procter & Gamble Company, Cincinnati, Ohio

[21] Appl. No.: 947,062

[22] Filed: Dec. 29, 1986

[51] Int. Cl.[4] .................. C07H 13/06; C07H 1/00; C08B 37/00

[52] U.S. Cl. ...................... 536/124; 536/119

[58] Field of Search .................. 536/119, 124

[56] References Cited

U.S. PATENT DOCUMENTS

| | | | |
|---|---|---|---|
| 2,013,034 | 9/1935 | Cox et al. | 536/119 |
| 2,812,324 | 12/1957 | Huber et al. | 536/119 |
| 2,831,854 | 4/1958 | Tucker et al. | 536/119 |
| 2,831,855 | 4/1958 | Tucker et al. | 536/119 |
| 2,831,856 | 4/1958 | Tucker et al. | 536/119 |
| 2,893,990 | 7/1959 | Hass et al. | 536/119 |
| 2,948,717 | 8/1960 | Babayan et al. | 536/119 |
| 3,021,324 | 2/1962 | Knafo et al. | 536/119 |
| 3,054,789 | 8/1962 | D'Amato | 536/119 |
| 3,096,324 | 7/1963 | Goins | 536/119 |
| 3,248,381 | 5/1966 | Nobile et al. | 536/119 |
| 3,251,827 | 5/1966 | Schnell et al. | 536/119 |
| 3,347,848 | 2/1967 | Ismail et al. | 536/119 |
| 3,349,081 | 2/1967 | Nobile | 536/119 |
| 3,558,597 | 1/1971 | Brachel et al. | 536/119 |
| 3,600,186 | 8/1971 | Mattson | 536/119 |
| 3,714,144 | 1/1973 | Feuge et al. | 536/119 |
| 3,775,503 | 11/1973 | Driscoll et al. | 585/16 |
| 3,792,041 | 2/1974 | Yamagishi et al. | 536/119 |
| 3,886,219 | 5/1975 | Reich | 568/881 |
| 3,954,976 | 3/1976 | Mattson et al. | 514/23 |
| 3,963,699 | 6/1976 | Rizzi et al. | 536/119 |
| 3,996,206 | 12/1976 | Parker et al. | 536/119 |
| 4,005,195 | 11/1977 | Jandacek | 514/23 |
| 4,005,196 | 11/1977 | Jandacek et al. | 514/23 |
| 4,034,083 | 11/1977 | Mattson | 514/23 |
| 4,241,054 | 12/1980 | Volpenhein et al. | 536/119 |
| 4,368,213 | 1/1983 | Hollenbach et al. | 426/590 |
| 4,461,782 | 7/1984 | Robbins et al. | 426/549 |
| 4,517,360 | 5/1985 | Volpenhein | 536/119 |
| 4,518,772 | 3/1985 | Volpenhein | 536/119 |
| 4,611,055 | 11/1986 | Yamamoto et al. | 536/119 |
| 4,705,690 | 11/1987 | Brand et al. | 536/119 |

OTHER PUBLICATIONS

Swern, Bailey's Industrial Oil & Fat Products, 3d Ed. Interscience Publishers, pp. 806–808 (1964).

*Primary Examiner*—Ronald W. Griffin
*Attorney, Agent, or Firm*—Gary M. Sutter; Eric W. Guttag; Richard C. Witte

[57] ABSTRACT

The invention is a process for post-hydrogenating sucrose polyesters with hydrogen gas in the presence of a catalytically effective amount of hydrogenation catalyst, at a temperature of from about 250° F. (121° C.) to about 450° F. (232° C.). Post-hydrogenation can be used to make sucrose polyesters that are different from those made by esterification. Preferably, the hydrogen pressure is at least about 20 psig. Increased hydrogen pressure overcomes steric hindrance of certain kinds of sucrose polyester molecules, allowing more complete hydrogenation of the fatty acids.

10 Claims, No Drawings

PROCESS FOR THE POST-HYDROGENATION OF SUCROSE POLYESTERS

FIELD OF THE INVENTION

The field of this invention is fatty acid esters of sucrose. In particular, the invention relates to a process for hydrogenating the unsaturated fatty acids of the sucrose polyesters after they have been esterified to the sucrose molecules.

BACKGROUND OF THE INVENTION

Hydrogenation consists of the addition of hydrogen to the double bonds of fatty acids, increasing the saturation of the fatty acids. In the hydrogenation of triglycerides, the reaction typically takes place by contacting triglyceride with gaseous hydrogen at a temperature above about 302° F. (150° C.), in the presence of a solid catalyst. It is known that increasing the pressure increases the rate of the triglyceride hydrogenation reaction. Swern, *Bailey's Industrial Oil and Fat Products*, Vol. 2, 4th ed., Interscience Publishers, NY, pp. 5–69 (1982), discusses the hydrogenation process in general.

Fatty acid esters of sucrose ("sucrose polyesters") are usually synthesized by one of three methods: transesterification of the sucrose with methyl, ethyl or glycerol fatty acid esters; acylation with a fatty acid chloride; or acylation with a fatty acid per se. As an example, the preparation of sucrose fatty acid polyesters is described in U.S. Pat. Nos. 2,831,854 and 3,521,827 (herein incorporated by reference).

More highly saturated sucrose polyesters are generally made by using more saturated fatty acids as the starting material prior to esterification. The present invention, on the other hand, concerns a method for increasing the saturation of sucrose polyesters by hydrogenating the polyesters after they have been synthesized from sucrose and fatty acids, i.e., "post-hydrogenation".

It is, therefore, an object of the present invention to provide an effective process for the post-hydrogenation of sucrose polyesters.

It is another object of the present invention to use the post-hydrogenation process to make sucrose polyesters that are different from those made by esterification alone.

It is a further object of the present invention to provide a post-hydrogenation process that allows more complete hydrogenation of certain kinds of sucrose polyester molecules.

These and other objects of the invention will be made clear by the disclosure herein.

All percentages are by weight unless otherwise defined.

SUMMARY OF THE INVENTION

The invention is a process for post-hydrogenating sucrose polyesters with hydrogen gas in the presence of a catalytically effective amount of hydrogenation catalyst, at a temperature of from about 250° F. (121° C.) to about 450° F. (232° C.). Post-hydrogenation can be used to make sucrose polyesters that are different from those made by esterification. Preferably, the hydrogen pressure is at least about 20 psig. Increased hydrogen pressure overcomes steric hindrance of certain kinds of sucrose polyester molecules, allowing more complete hydrogenation of the fatty acids.

DETAILED DESCRIPTION OF THE INVENTION

The present invention is concerned with the post-hydrogenation of sucrose polyesters, i.e., hydrogenation of the fatty acids of sucrose polyesters after the fatty acids are already esterified to the sucrose molecules.

Post-hydrogenation of sucrose polyesters allows the synthesis of polyesters that are different from those made by esterification alone. When sucrose is esterified with fatty acids, different kinds of fatty acids will preferentially esterify to particular sites on the sucrose molecule depending on their degree of unsaturation and other factors. When these fatty acids are post-hydrogenated, the resulting more saturated fatty acids often are positioned on the sucrose at positions different than would have resulted had these fatty acids been first hydrogenated and then esterified to sucrose. Hence, post-hydrogenation can produce sucrose polyesters with differently positioned fatty acids, giving the polyesters different physical attributes. In particular, sucrose polyesters with specific unique melt profiles can be produced. Samples of sucrose polyester made by post-hydrogenation and by transesterification having similar iodine values were found to have very different Solid Fat Content (SFC) curves.

The process of this invention for post-hydrogenating sucrose fatty acid polyesters comprises contacting the sucrose polyesters with hydrogen gas in the presence of a catalytically effective amount of hydrogenation catalyst, at a temperature of from about 250° F. (121° C.) to about 450° F. (232° C.). In ordinary practice the hydrogen is first brought into contact with the polyesters, with the hydrogen-laden polyesters then brought into contact with the catalyst by mechanical means. In the usual type of equipment, a suspension of catalyst and polyester is agitated in a closed vessel in an atmosphere of hydrogen. Agitation of the catalyst-polyester mixture promotes dissolution of hydrogen in the polyester and continuously renews the polyester at the catalyst surface. For a thorough discussion of hydrogenation equipment, see Swern, *Bailey's Industrial Oil and Fat Products*, Vol. 2, 4th ed., Interscience Publishers, NY, pp. 27–37 (1982).

The sucrose polyesters employed in this invention comprise well-defined sucrose fatty acid esters. Sucrose has eight esterifiable hydroxyl groups. The sucrose fatty acid esters useful in this invention must contain at least four fatty acid ester groups. Sucrose fatty acid ester compounds that contain three or less fatty acid ester groups tend to be digested in the intestinal tract in much the same manner as ordinary triglyceride fats, whereas the sucrose fatty acid ester compounds that contain four or more fatty acid ester groups are substantially non-absorbable and non-digestible by the human body. It is not necessary that all of the hydroxyl groups of the sucrose be esterified with fatty acid, but it is preferable that the sucrose polyester contain no more than three unesterified hydroxyl groups, and more preferably no more than two unesterified hydroxyl groups. The fatty acid ester groups can be the same or mixed on the same sucrose polyester molecule.

The sucrose starting material must be esterified with fatty acids having from about eight to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. Of course, at least one of the fatty acids must be unsaturated for the process of this invention to be useful.

Fatty acids per se or naturally occurring fats and oils can serve as the source of the fatty acid component in the sucrose fatty acid ester. For example, rapeseed oil provides a good source for $C_{22}$ fatty acid. $C_{16}$-$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, seasame seed oil, and sunflower seed oil, are examples of other natural oils which can serve as the source of the fatty acid component.

The catalyst can be any standard hydrogenation catalyst. The preferred catalyst is nickel metal, although minor amounts of copper, aluminum, etc., can be incorporated with the nickel for their "promoter" or selectivity action. Other catalysts include metals, alloys and compounds of, for example, chromium, cobalt, copper, iron, lead, manganese, mercury, molybdenum, palladium, platinum, thorium, titanium, vanadium, zinc and zirconium. Preferably, the catalyst is present in the amount of from about 0.01% to about 0.5% by weight of the sucrose polyester. The amount of catalyst used is dependent upon the rate of reaction to be attained and other variables such as temperature and pressure, and the starting polyesters.

A preferred method for preparing the catalyst is to mix from about 15% to about 28% nickel catalyst into liquid triglyceride or liquid sucrose polyester.

Hydrogenation is carried out at a temperature of from about 250° F. (121° C.) to about 450° F. (232° C.). The preferred temperature range is from about 340° F. (171° C.) to about 410° F. (210° C.), and the most preferred range is from about 365° F. (185° C.) to about 405° F. (207° C.).

The time of hydrogenation is a function of the temperature, pressure, type of sucrose polyester, and most importantly, the type of catalyst. The sucrose polyester is hydrogenated to a particular Refractive Index endpoint (as an indicator of Iodine Value), depending on the kind of product desired.

Triglycerides are generally hydrogenated until the product reaches a particular Refractive Index, which is correlated with Iodine Value, a measure of the degree of unsaturation of the triglycerides. It was attempted to hydrogenate sucrose polyesters at atmospheric pressure to a certain Refractive Index. Surprisingly, it was found that the Refractive Index reached a point beyond which it changed no further, even with additional hydrogenation time. The problem, it has now been found, is that unlike the hydrogenation of triglycerides, the hydrogenation of sucrose polyesters is to a great extent affected by steric hindrance of the fatty acids on the sucrose molecules. The shape of certain kinds of sucrose fatty acid ester molecules is such that it is impossible to hydrogenate some of the fatty acid unsaturation sites under normal conditions. For example, the hydrogenation process did not hydrogenate the 9-10 carbon double bond of a sucrose polyester, resulting in a polyester which was high in mono-unsaturates.

It has now been discovered that post-hydrogenating the sucrose polyesters under high pressure can overcome the problems caused by steric hindrance. This is an unexpected finding based on what is known of triglyceride hydrogenation because, while increased pressure increases the rate of hydrogenation of triglycerides, increased pressure does not change the extent of hydrogenation of the triglycerides. By contrast, post-hydrogenation of sucrose polyesters under high pressure can produce sucrose polyesters that are hydrogenated to a greater extent. For example, post-hydrogenation under pressure enabled hydrogenation of the 9-10 carbon double bond of the sucrose polyester fatty acids.

Hence, although the process of the present invention can be conducted at atmospheric pressure, a preferred embodiment of the present invention is to post-hydrogenate the sucrose polyesters under a hydrogen pressure of at least about 20 psig. More preferably, the hydrogen pressure will be at least about 40 psig, and most preferably the pressure will be at least about 45 psig.

ANALYTICAL METHODS

Solid Fat Content: The method for determining Solid Fat Content (SFC) values of a fat by PNMR is described in Madison and Hill, *J. Amer. Oil Chem. Soc.*, Vol. 55 (1978), pp. 328-31 (herein incorporated by reference). Before determining SFC values, the fat material sample is heated to a temperature of 158° F. (70° C.) or higher for at least 0.5 hours or until the sample is completely melted. The melted sample is then tempered at a temperature of 40° F. (4° C.) for at least 72 hours. After tempering, the SFC value of the fat material at a temperature of 100° F. (38° C.) is determined by pulsed nuclear magnetic resonance (PNMR).

Fatty Acid Composition: The fatty acid composition is determined by gas chromatography, utilizing a Hewlett-Packard Model S712A gas chromatograph equipped with a thermal conductivity detector and a Hewlett-Packard Model 7671A automatic sampler. The chromatographic method utilized is described in *Official Methods and Recommended Practices of the American Oil Chemists Society*, 3rd Ed., 1984, Procedure Ce1-62.

The following examples are intended only to further illustrate the invention and are not intended to limit the scope of the invention which is defined by the claims.

EXAMPLE 1

Forty pounds of a sucrose polyester made by transesterifying sucrose with soy-based methyl esters is placed into a 50-lb. stainless steel reaction vessel at 150° F. (66° C.). The reaction vessel is sparged with nitrogen at atmospheric pressure and heated to a temperature of 350° F. (177° C.) over a period of 65 minutes. Next, 80 g. of a slurry made with 17.5 g. nickel metal catalyst and 62.5 g. coconut oil hardstock is added to the polyester. Then hydrogen is introduced into the reaction vessel at a pressure of 50 psig. The temperature is raised to 400° F. (204° C.) over a 45-minute period, and then the hydrogenation reaction is continued at this temperature for 1 hour and 10 minutes until the Refractive Index of the product is 51.9. After the reaction is completed, the vessel is depressurized to atmospheric pressure and sparged with nitrogen gas, and the reaction mixture is quickly cooled to 200° F. (93° C.) and then filtered.

The hydrogenated sucrose polyester product has the following fatty acid composition and Solid Fat Content:

| FAC: | C12 | 0.1% |
|---|---|---|
| | C14 | 0.1% |

|     |                |       |
| --- | -------------- | ----- |
|     | C16            | 10.2% |
|     | C18            | 24.5% |
|     | C18-1          | 56.1% |
|     | C18-2          | 7.4%  |
|     | C18-3          | 0.6%  |
|     | C20            | 0.7%  |
|     | C22            | 0.3%  |
| SFC: | 50° F. (10° C.): | 47.9% |
|     | 70° F. (21° C.): | 24.7% |
|     | 80° F. (27° C.): | 20.6% |
|     | 92° F. (33° C.): | 13.2% |
|     | 105° F. (41° C.): | 6.8% |

The product's Refractive Index is 51.9, and its Iodine Value is 62.2.

EXAMPLE 2

Two samples of sucrose polyester are made. The first sample is synthesized by transesterification. The second sample is also made by transesterification, but the polyester is also post-hydrogenated after esterification:

A. First sucrose polyester, made by transesterification:

Soy-based methyl esters with an Iodine Value of 40.4 (227.3 kg.), and 36 kg. of an 18 wt. percent solution of potassium hydroxide in methanol are mixed in a stainless steel batch reactor. This mixture is then heated to 122° F. (50° C.) with agitation for 1 to 2 hours at atmospheric pressure. During this time, a portion of the methyl esters are saponified. A vacuum is then pulled on the system to remove the last traces of methanol.

Granular sucrose (45.5 kg.) is added to the soap/ester mixture to give a 5:1 molar ratio of ester to sucrose. Potassium carbonate is then added to the mixture (approx. 0.5 wt. percent of the reaction mix) to catalyze the transesterification. This mixture is agitated and heated under vacuum at about 275° F. (135° C.) for up to 8 hours to form the mono-, di- and trisucrose esters. Small quantities of tetra- and pentaesters are also formed during this stage. Additional methyl ester (276.7 kg.) which has been preheated to 275° F. (135° C.) is added to bring and maintain the molar ratio of the esters to sucrose to 12:1. When the reaction conditions stabilize at 275° F. (135° C.), a nitrogen sparge is used to improve agitation and promote methanol stripping. As the reaction occurs, the reaction mixture becomes viscous and then thins out. This second reaction stage lasts approximately 24 to 36 hours.

After the reaction mixture has become thin, it is cooled to between 149° F. (65° C.) and 185° F. (85° C.). The crude reaction mixture is agitated with a dilute solution of methanol, sodium chloride and water. The volume of this wash solution is equal to 20% to 40% of the reaction mixture volume. The mixed phases are then allowed to settle for approximately 30 to 60 minutes. The lower settled phase which contains the soaps, excess sugars and methanol is drawn off and discarded. The settled phase which comprises the refined sucrose polyesters is washed again. Usually 2 to 4 washes are used.

The sucrose polyesters are then washed with a 1% glacial acetic acid in water solution at 10% to 20% of the volume of the reaction mix. This is followed by water wash of the same volume.

The reaction mix is then dried under vacuum. The reaction mixture is then treated with an oil bleaching agent and filtered. The bulk of the unreacted methyl esters are removed by distillation at 374° F. (190° C.) to 482° F. (250° C.) under approximately 5 mm Hg of vacuum.

The sucrose polyester is then deodorized in a stainless steel batch deodorizer or other suitable device at 374° F. (190° C.) to 482° F. (250° C.) under a vacuum of about 5 mm Hg with steam sparging. Deodorization is continued until the methyl ester content is below 200 ppm. The deodorizer contents are then cooled to 149° F. (65° C.) while using inert gas sparging. The sucrose polyester is stored in clean stainless steel drums.

This produces a sucrose polyester product having the following properties:

|     |                |       |
| --- | -------------- | ----- |
| FAC: | C12           | 0%    |
|     | C14            | 0%    |
|     | C16            | 13.2% |
|     | C18            | 42.8% |
|     | C18-1          | 40.1% |
|     | C18-2          | 3.9%  |
|     | C18-3          | 0%    |
|     | C20            | 0%    |
|     | C22            | 0%    |
| SFC: | 50° F. (10° C.): | 72.9% |
|     | 70° F. (21° C.): | 59.3% |
|     | 80° F. (27° C.): | 45.3% |
|     | 92° F. (33° C.): | 22.9% |
|     | 105° F. (41° C.): | 9.2% |

The product's Iodine Value is 41.3.

B. Second sucrose polyester, made by post-hydrogenation after transesterification:

Twenty-six pounds of a sucrose polyester made by transesterifying sucrose with soy-based methyl esters having an Iodine Value of about 107 is placed into a stainless steel reaction vessel. The reaction vessel is sparged with nitrogen at atmospheric pressure and heated to a temperature of 360° F. (182° F.) over a period of 85 minutes. Next, 60 g. of a slurry made with 13.2 g. nickel metal catalyst and 46.8 g. of a melted coconut oil hardstock is added to the polyester. Then hydrogen is introduced into the reaction vessel at atmospheric pressure. The temperature is raised to 400° F. (204° C.), and then the hydrogenation reaction is continued at this temperature for 6 hours and 30 minutes until the Refractive Index of the product is 46.3. After the reaction is completed, the hydrogen is shut off and the vessel is sparged with nitrogen gas, and the reaction mixture is quickly cooled to 200° F. (93° C.) and then filtered.

The post-hydrogenated sucrose polyester product has the following fatty acid composition and Solid Fat Content:

|     |                |       |
| --- | -------------- | ----- |
| FAC: | C12           | 0.3%  |
|     | C14            | 0%    |
|     | C16            | 11.9% |
|     | C18            | 42.9% |
|     | C18-1          | 44.9% |
|     | C18-2          | 0%    |
|     | C18-3          | 0%    |
|     | C20            | 0%    |
|     | C22            | 0%    |
| SFC: | 50° F. (10° C.): | greater than 85% |
|     | 70° F. (21° C.): | greater than 85% |
|     | 80° F. (27° C.): | greater than 85% |
|     | 92° F. (33° C.): | greater than 85% |
|     | 105° F. (41° C.): | greater than 85% |

The Solid Fat Content of the sucrose polyester is too solid for measurement at all temperatures. The product's Refractive Index is 46.3 and its Iodine Value is 38.6.

The first sucrose polyester, made by transesterification alone, has an Iodine Value of 41.3 and the second sucrose polyester, made by post-hydrogenation following transesterification, has an Iodine Value of 38.6. This is true even though the polyesters were synthesized from soy-based methyl esters having Iodine Values of about 40 and about 107, respectively. While the Iodine Values for the two sucrose polyester products are similar, the Solid Fat Content curves of the polyesters are very different.

What is claimed is:

1. A process for post-hydrogenating sucrose polyesters comprising contacting sucrose polyesters having at least one unsaturated fatty acid with hydrogen gas in the presence of a catalytically effective amount of hydrogenation catalyst, at a temperature of from about 250° F. (121° C.) to about 450° F. (232° C.) to hydrogenate the unsaturated fatty acids of the sucrose polyesters.

2. A process according to claim 1 wherein the temperature is from about 340° F. (171° C.) to about 410° F. (210° C.).

3. A process according to claim 2 wherein the temperature is from about 365° F. (185° C.) to about 405° F. (207° C.).

4. A process according to claim 1 wherein the amount of catalyst is from about 0.01% to about 0.5% by weight of the sucrose polyester.

5. A process according to claim 1 wherein the catalyst is nickel metal.

6. A process according to claim 1 wherein the hydrogen is under a pressure of at least about 20 psig.

7. A process according to claim 6 wherein the pressure is at least about 40 psig.

8. A process according to claim 7 wherein the pressure is at least about 45 psig.

9. The product of the process of claim 1 having an Iodine Value of from 38.6 to 62.2.

10. The product of the process of claim 6 having an Iodine Value of from 38.6 to 62.2.

* * * * *